US010363172B2

(12) United States Patent
Kawai et al.

(10) Patent No.: US 10,363,172 B2
(45) Date of Patent: Jul. 30, 2019

(54) OPHTHALMIC LASER TREATMENT APPARATUS

(71) Applicant: NIDEK CO., LTD., Gamagori-shi, Aichi (JP)

(72) Inventors: Masato Kawai, Okazaki (JP); Seiki Tomita, Gamagori (JP)

(73) Assignee: NIDEK CO., LTD., Gamagori-shi (JP)

( * ) Notice: Subject to any disclaimer, the term of this patent is extended or adjusted under 35 U.S.C. 154(b) by 182 days.

(21) Appl. No.: 15/053,519

(22) Filed: Feb. 25, 2016

(65) Prior Publication Data

US 2016/0250075 A1 Sep. 1, 2016

(30) Foreign Application Priority Data

Feb. 26, 2015 (JP) ................. 2015-036413

(51) Int. Cl.
*A61F 9/008* (2006.01)
*A61B 18/20* (2006.01)

(52) U.S. Cl.
CPC .......... *A61F 9/00825* (2013.01); *A61B 18/20* (2013.01); *A61F 9/008* (2013.01); *A61F 2009/00844* (2013.01); *A61F 2009/00868* (2013.01); *A61F 2009/00874* (2013.01); *A61F 2009/00876* (2013.01); *A61F 2009/00887* (2013.01)

(58) Field of Classification Search
CPC ......... A61B 18/042; A61B 2018/00988; A61F 9/008; A61F 2009/00887; A61F 2009/0087; A61F 2009/00897
USPC .............................................. 606/4–6, 10–13
See application file for complete search history.

(56) References Cited

U.S. PATENT DOCUMENTS 6,325,793 B1 * 12/2001 Tomita ................... A61F 9/008
606/10
6,346,100 B1 2/2002 Tano et al.
(Continued)

FOREIGN PATENT DOCUMENTS

JP H03-118060 A 5/1991
JP H11-332905 A 12/1999
JP 2008-183247 A 8/2008

OTHER PUBLICATIONS

Jul. 18, 2016 Extended Search Report issued in European Patent Application No. 16157321.7.

*Primary Examiner* — David Shay
(74) *Attorney, Agent, or Firm* — Oliff PLC

(57) ABSTRACT

An ophthalmic laser treatment apparatus includes: an aiming optical system configured to irradiate an aiming beam to a patient's eye; a laser irradiation optical system configured to irradiate a laser beam for treatment to the patient's eye; a shift unit configured to make a shift of a focus shift position corresponding to a focus position of the laser beam to a posterior or anterior position with respect to a focus position of the aiming beam; a selection receiving unit configured to receive an instruction to select any one of a plurality of treatment modes; and a control unit configured to control operations of the ophthalmic laser treatment apparatus. The control unit sets a value of a parameter related to irradiation of the laser beam, the parameter including a parameter related to the shift of the focus shift position, according to the treatment mode selected with the selection receiving unit.

10 Claims, 8 Drawing Sheets

(56) References Cited

U.S. PATENT DOCUMENTS

| | | | | |
|---|---|---|---|---|
| 6,652,511 B1 * | 11/2003 | Tomita | ................... | A61F 9/008 606/4 |
| 8,066,696 B2 | 11/2011 | Abe | | |
| 2006/0224147 A1 | 10/2006 | Abe et al. | | |
| 2007/0213693 A1 * | 9/2007 | Plunkett | ................. | A61F 9/008 606/6 |

* cited by examiner

OPHTHALMIC LASER TREATMENT APPARATUS

CROSS-REFERENCE TO RELATED APPLICATIONS

This application is based upon and claims the benefit of priority from the prior Japanese Patent Application No. 2015-036413 filed on Feb. 26, 2015, the entire contents of which are incorporated herein by reference.

BACKGROUND

The present invention relates to an ophthalmic laser treatment apparatus for irradiating a laser beam for treatment to a patent's eye.

Conventionally, there has been known an ophthalmic laser treatment apparatus for irradiating a laser beam for treatment to a patient's eye. For example, an ophthalmic laser treatment apparatus disclosed in Japanese unexamined patent application publication No. 3(1991)-118060 includes a convergent-point position adjusting optical system configured to displace a convergent point position of a treatment laser beam forward by a desired distance with respect to a convergent point position of an aiming beam in order to align a convergent point of a YAG laser beam with a position separated by a desired distance from an internal surface of an opaque body.

SUMMARY

There are cases where a single ophthalmic laser treatment apparatus is used for treatment of various disease cases (e.g., secondary cataract, iridotomy, etc.). With such an apparatus, it is troublesome for an operator or surgeon to change irradiation conditions (settings) of a laser beam for treatment according to types of disease cases and others. Further, the operator may incorrectly set the irradiation conditions.

The present disclosure has a purpose to provide an ophthalmic laser treatment apparatus with which irradiation conditions of a treatment laser beam can be easily set.

To achieve the foregoing purpose, one aspect of the present disclosure provides an ophthalmic laser treatment apparatus comprising: an aiming optical system configured to irradiate an aiming beam to a patient's eye; a laser irradiation optical system configured to irradiate a laser beam for treatment to the patient's eye; a shift unit configured to make a shift of a focus shift position corresponding to a focus position of the laser beam to a posterior or anterior position with respect to a focus position of the aiming beam; a selection receiving unit configured to receive an instruction to select any one of a plurality of treatment modes; and a control unit configured to control operations of the ophthalmic laser treatment apparatus, wherein the control unit sets a value of a parameter related to irradiation of the laser beam, the parameter including a parameter related to the shift of the focus shift position, according to the treatment mode selected with the selection receiving unit.

The present disclosure can provide an ophthalmic laser treatment apparatus with which irradiation conditions of a treatment laser beam can be easily set.

DETAILED DESCRIPTION OF THE EXEMPLARY EMBODIMENTS

Figure 1:
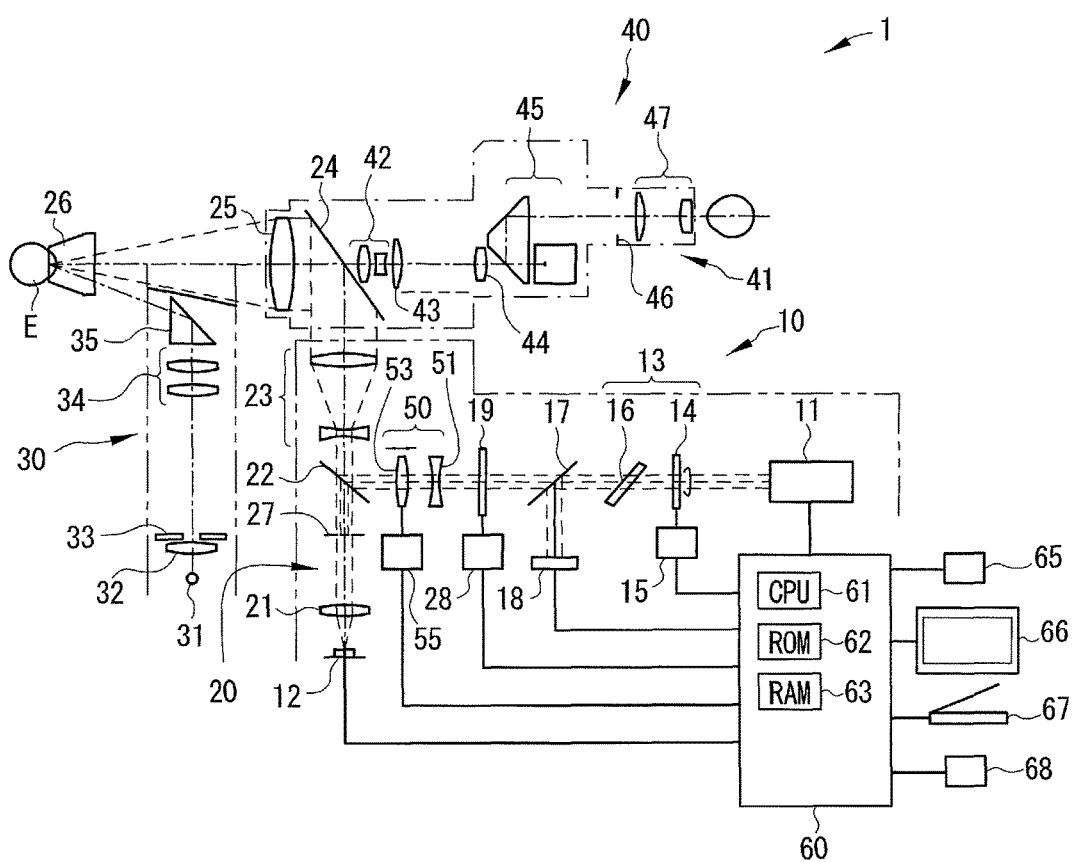
FIG. 1 is a schematic diagram showing an ophthalmic laser treatment apparatus in an embodiment.

Hereinafter, one of typical embodiments of this disclosure will be described below referring to accompanying drawings. Referring to FIG. 1, a schematic configuration view of an ophthalmic laser treatment apparatus 1 in the present embodiment will be first explained. The ophthalmic laser treatment apparatus 1 in the present embodiment includes, as one example, a laser irradiation optical system 10, an aiming optical system 20, an illumination optical system 30, an observation optical system 40, and a control unit 60.

<Laser Irradiation Optical System>

The laser irradiation optical system 10 in the present embodiment includes a laser source 11, an energy adjusting unit 13, a beam splitter 17, a light detector 18, a safety shutter 19, a shift adjusting unit 50, a dichroic mirror 22, expander lenses 23, a dichroic mirror 24, and an objective lens 25.

The laser source 11 emits a laser beam for treatment (hereinafter, referred to as a "treatment laser beam") to treat tissues of a patient's eye E. As one example, this laser source 11 in the present embodiment is provided with a YAG (yttrium aluminum garnet) crystal doped with neodymium as a laser rod. A wavelength conversion element not shown can convert an infrared laser beam (wavelength: 1064 nm) emitted from the laser source 11 into a visible laser beam (wavelength: 532 nm)

The energy adjusting unit 13 adjusts an energy amount of the treatment laser beam to be irradiated to the tissues of the patient' eye E. The energy adjusting unit 13 in the present embodiment includes a ½ wave plate 14 and a polarization plate 16. The ½ wave plate 14 is rotated about an optical axis of the treatment laser beam by a motor 15. The polarization plate 16 is placed at a Brewster angle. These ½ wave plate 14 and polarization plate 16 are combined to adjust the energy amount of the treatment laser beam.

The beam splitter 17 reflects part of the treatment laser beam toward the light detector 18. This light detector 18 receives the treatment laser beam reflected by the beam splitter 17 to detect the energy amount of the treatment laser beam. The safety shutter 19 is moved on and off the optical axis of the treatment laser beam by a shutter drive unit 28 (e.g., a solenoid). This safety shutter 19 is disposed on the optical axis of the treatment laser beam to block irradiation of the treatment laser beam to the patient's eye E.

The expander lenses 23 expand a light beam of the light wave-combined by the dichroic mirror 22 (the treatment laser beam and an aiming beam described later). The light expanded by the expander lenses 23 is reflected by the dichroic mirror 24 and allowed to pass through the objective lens 25. In the present embodiment, the treatment laser beam having passed through the objective lens 25 is then irradiated to the tissues of the patient's eye E through a contact lens 26 worn on the eye E. To avoid reflection light of the treatment laser beam reflected by the patient's eye E from entering an operator, the dichroic mirror 24 reflects almost all the light at wavelengths of the reflection light. The laser irradiation optical system 10 may be provided with a structure for adjusting a spot size of the treatment laser beam to be irradiated to the tissues, and other structures.

<Aiming Optical System>

The aiming optical system 20 in the present embodiment is used for aiming at a target portion to be treated. Specifically, the aiming optical system 20 in the present embodiment is used as an aiming unit for irradiating an aiming beam for aiming at a portion targeted for treatment. The aiming optical system 20 in the present embodiment includes an aiming source 12, a collimator lens 21, an aperture plate 27, the dichroic mirror 22, the expander mirrors 23, the dichroic mirror 24, and the objective lens 25. The aiming optical system 20 in the present embodiment shares an optical path produced beyond the dichroic mirror 22 (an optical path produced from the dichroic mirror 22 to the objective lens 25, in terms of components constituting the ophthalmic laser treatment apparatus 1), with the foregoing laser irradiation optical system 10.

The aiming source 12 emits an aiming beam to allow an operator to guide a position to be irradiated by a treatment laser beam (that is, a position of a treatment spot). In the present embodiment, as this aiming source 12, a light source that emits a visible laser beam having a wavelength of 635 nm (red) is used. However, needless to say, the wavelength of the aiming beam and others may be appropriately changed. For example, the aiming source 12 may also be selected from a LED, a SLD, and other light sources.

The collimator lens 21 collimates the aiming beam emitted from the aiming source 12 into a parallel beam. The aperture plate 27 in the present embodiment splits the parallel aiming beam collimated by the collimator lens 21 into two beams. More specifically, the aperture plate 27 in the present embodiment is formed with two apertures. These two apertures are arranged symmetric with respect to the optical axis of the aiming optical system 20. The dichroic mirror 22 combines the treatment laser beam and the aiming beam. In the present embodiment, the dichroic mirror 22 reflects the treatment laser beam and transmits the aiming beam to combine the treatment laser beam and the aiming beam. The ophthalmic laser treatment apparatus 1 may be arranged to irradiate the treatment laser beam and the aiming beam to the patient's eye E from separate optical paths without combining those beams.

The aiming beam emitted from the aiming source 12 as described above is split into two beams by the aperture plate 27 and then concentrated at a forward focus position of the objective lens 25. On that focus position (a focus plane), the beams split by the aperture plate 27 overlap into one. At forward and backward positions (a defocus plane) with respect to the focus position of the aiming beam, the aiming beam remains split (beams). Accordingly, the operator can easily check an alignment state of the aiming beam (in an anterior-posterior direction) from the split state of the aiming beam.

<Shift Unit>

The ophthalmic laser treatment apparatus 1 in the present embodiment is provided with a shift unit. This shift unit is configured to displace (shift) the focus position of the treatment laser beam emitted from the laser source 11 with respect to the focus position of the aiming beam emitted from the aiming source 12. The shift unit in the present embodiment can displace the focus position emitted from the laser source 11 to either a posterior position or an anterior position with respect to the focus position of the aiming beam. In the following description, the focus position of the treatment laser beam with respect to the focus position of the aiming beam may be also referred to as a focus shift position. When the focus shift position is expressed by a numerical value, a focus shift position located more anteriorly than the focus position of the aiming beam (in a direction to come close to the objective lens 25) may be indicated with a negative sign and a focus shift position located more posteriorly than the focus position of the aiming beam (in a direction to go away from the objective lens 25) may be indicated with a positive sign. In other words, the anterior position (the posterior position) is located on an upstream side (a downstream side) or a near side (a far side) in a direction along the optical path of the treatment laser beam.

In the present embodiment, the shift adjusting unit 50 is used as a shift unit. This shift adjusting unit 50 includes a concave lent 51 and a convex lens 53. The ophthalmic laser treatment apparatus 1 in the present embodiment is further provided with a drive unit for driving the shift adjusting unit 50 to shift the focus shift position. In the present embodiment, a motor 55 is used as the drive unit. The motor 55 may be for example a stepping motor. In the present embodiment, the motor 55 is connected to the convex lens 53 and also is connected to the control unit 60. Thus, the control unit 60 can adjust the focus shift position. In short, the ophthalmic laser treatment apparatus 1 in the present embodiment is provided with an adjustment unit for adjusting the focus shift position. In the present embodiment, the control unit 60 moves the convex lens 53 in an optical axis direction. The adjustment unit in the present embodiment can adjust the focus shift position in a range of $-500$ μm to $+500$ μm.

<Illumination Optical System>

The illumination optical system 30 in the present embodiment is configured to illuminate a portion being observed including the tissues targeted for treatment. The illumination optical system 30 in the present embodiment includes a lamp 31, a lens 32, a diaphragm 33, lenses 34, and a prism 35. For example, a white light emitting device or the like may be used as the lamp 31. It is to be noted that the illumination optical system 30 may be provided with a slit plate or the like to project slit light onto the observed portion.

<Observation Optical System>

The observation optical system 40 in the present embodiment is used for an operator to observe an observed portion of the patient eye E. The observation optical system 40 in the present embodiment is installed in a microscope 41 and is provided with a variable power optical system 42, an operator protection filter 43, an image forming lens 44, an erect prism group 45, a field diaphragm 46, and eyepieces 47. The dichroic mirror 24 and the objective lens 25 are shared between the laser irradiation optical system 10 and the observation optical system 40 and also shared between right and left observation optical paths (an optical path for a left eye and an optical path for a right eye of the operator) inside the microscope 41. Other components (the variable power optical system 42 and others) are individually provided in each of the right and left observation optical paths. The variable power optical system 42 is used to change the magnification of observation. For instance, a rotary drum or the like in which a plurality of lenses different in refractive power are combined can be used as the variable power optical system 42. The operator protection filter 43 has the property of attenuating the wavelength of the treatment laser beam. This operator protection filter 43 also serves to prevent the treatment laser beam reflected by the patient's eye and others from reaching operator's eyes.

<Control Unit>

The control unit 60 is one example of a control unit for controlling operations of the ophthalmic laser treatment apparatus 1. The control unit 60 in the present embodiment is provided with a CPU 61 (a processor), a ROM 62, a RAM 63, a nonvolatile memory 65, and others. The CPU 61 is responsible for control of each part or unit of the ophthalmic laser treatment apparatus 1. The ROM 62 has stored therein various programs, default values, and others. The ROM 63 temporarily stores various data. The nonvolatile memory 65 is a non-transitory storage medium that can hold memory content even if power supply is shut off. For example, the nonvolatile memory 65 may be selected from a USB memory which can be detachably mounted in the control unit 60, a flash ROM built in the control unit 60, and others. In the present embodiment, the nonvolatile memory 65 is used as a storage unit for storing parameters related to irradiation of the treatment laser beam. As the storage unit, the RAM 63, the ROM 62, or other state holding medium (e.g., a DIP switch or the like) may be used. The foregoing parameters will be further described in detail later.

The control unit 60 in the present embodiment is connected to the laser source 11, the motor 15, the light detector 18, the shutter drive unit 28, the motor 55, the aiming source 12, the lamp 31, a display unit 66, a trigger switch 67, a buzzer (or a beeper) 68, and others. The display unit 66 displays thereon various images. The control unit 60 in the present embodiment functions as a display control unit for controlling display of the display unit 66. The display unit 66 in the present embodiment has a touch panel function and thus is used as a display unit and an input unit. An operator or the like is allowed to enter various instructions by operating (touching) the surface of the display unit 66. The trigger switch 67 is operated by the operator to enter an instruction to execute irradiation of the treatment laser beam.

The buzzer 68 in the present embodiment is a notification unit for notifying the state of the ophthalmic laser treatment apparatus 1 to the operator (notification to the operator will be described later). The control unit 60 in the present embodiment functions as a notification control unit for controlling the notification unit. In the present embodiment, the buzzer 68 is used as the notification unit, but a notification method is not limited to the buzzer 68. For example, an LED may be used as the notification unit. As another alternative, a message may be displayed on the display unit 66 as the notification unit.

<Adjustable Range>

The control unit 60 in the present embodiment can adjust the irradiation energy amount of the treatment laser beam in a range of 0.3 mJ to 10.0 mJ. The control unit 60 can also adjust the focus shift position in a range of −500 μm to +500 μm. Further, the control unit 60 can adjust the number of bursts in a range of 1 to 3 (shots). This number of bursts represents the number of repeating times of irradiation of the treatment laser beam. Upon detection that the trigger switch 67 is depressed, the control unit 60 in the present embodiment causes the treatment laser beam to be irradiated by the number of times set as the number of bursts.

<Treatment Mode>

The ophthalmic laser treatment apparatus 1 in the present embodiment has a plurality of treatment modes as an operation mode of the ophthalmic laser treatment apparatus 1. In the present embodiment, the plurality of treatment modes include treatment modes corresponding to the types of disease cases. Specifically, the plurality of treatment modes include a plurality of treatment modes different in type of disease case. The ophthalmic laser treatment apparatus 1 in the present embodiment provides five treatment modes. To be specific, the ophthalmic laser treatment apparatus 1 in the present embodiment provides a standard mode (a first treatment mode), an secondary cataract mode (a second treatment mode), an iridotomy mode (a third treatment mode), a laser trabeculotomy mode (a fourth treatment mode), and a laser vitrectomy mode (a fifth treatment mode). In addition, the ophthalmic laser treatment apparatus 1 may provide other treatment modes.

Each of the treatment modes will be described below (also referring to FIGS. 3 and 5). The standard mode in the present embodiment is an operation mode of enabling an operator to widely set (adjust) parameters (irradiation conditions) related to irradiation of the treatment laser beam without subjecting to warning notification or limitation. The secondary cataract mode in the present embodiment is a treatment mode suitably used for treatment of secondary cataract. For instance, this secondary cataract mode is suitably used to irradiate the treatment laser beam to an opacified portion of a capsule of a patient's eye E generated after an intraocular lens is set in the capsule. The iridotomy mode in the present embodiment is a treatment mode suitably used to incise an iris for treatment. For instance, this iridotomy mode is suitably used to irradiate the treatment laser beam to an iris for treatment of reducing the intraocular pressure having increased due to glaucoma.

The laser trabeculotomy mode in the present embodiment is a treatment mode suitably used to incise trabecula for treatment. For instance, this laser trabeculotomy mode is suitably used to irradiate the treatment laser beam to clogged trabecular meshwork in order to allow aqueous fluid to flow through a Schlemm's canal for treatment of suppressing the progression of glaucoma. The laser vitrectomy mode is a treatment mode suitably used to remove or resect a vitreous body for treatment. For instance, this laser vitrectomy mode is suitably used for treatment of resecting a pulling portion of the vitreous body that pulls a retina.

<Display Unit and Input Unit>

Figure 2:
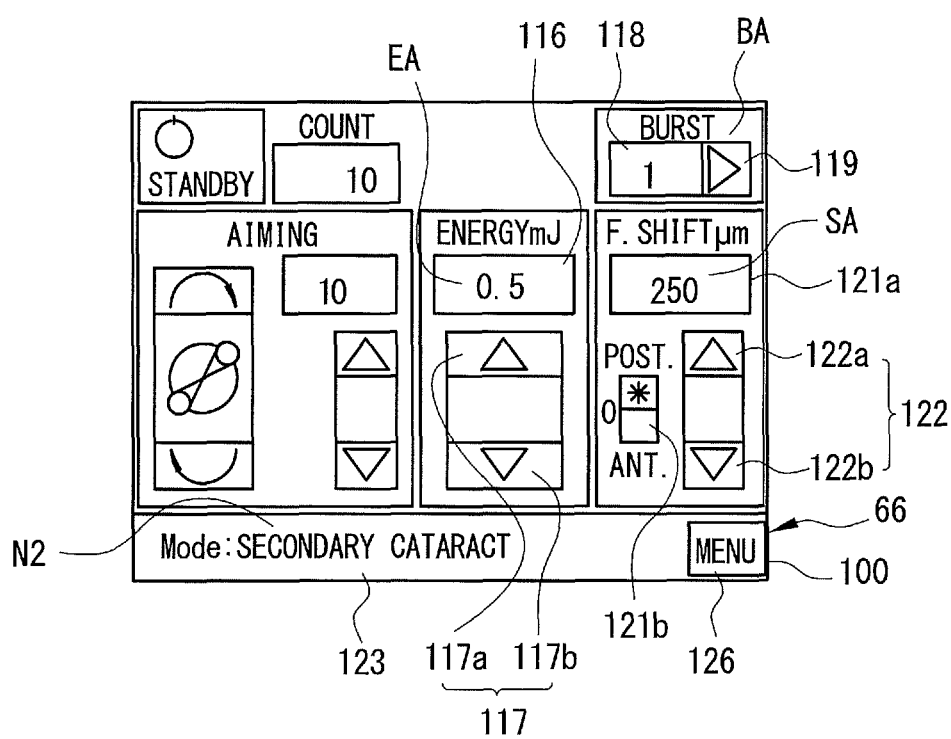
FIG. 2 is a diagram showing a treatment screen displayed on a display unit.
Figure 3:
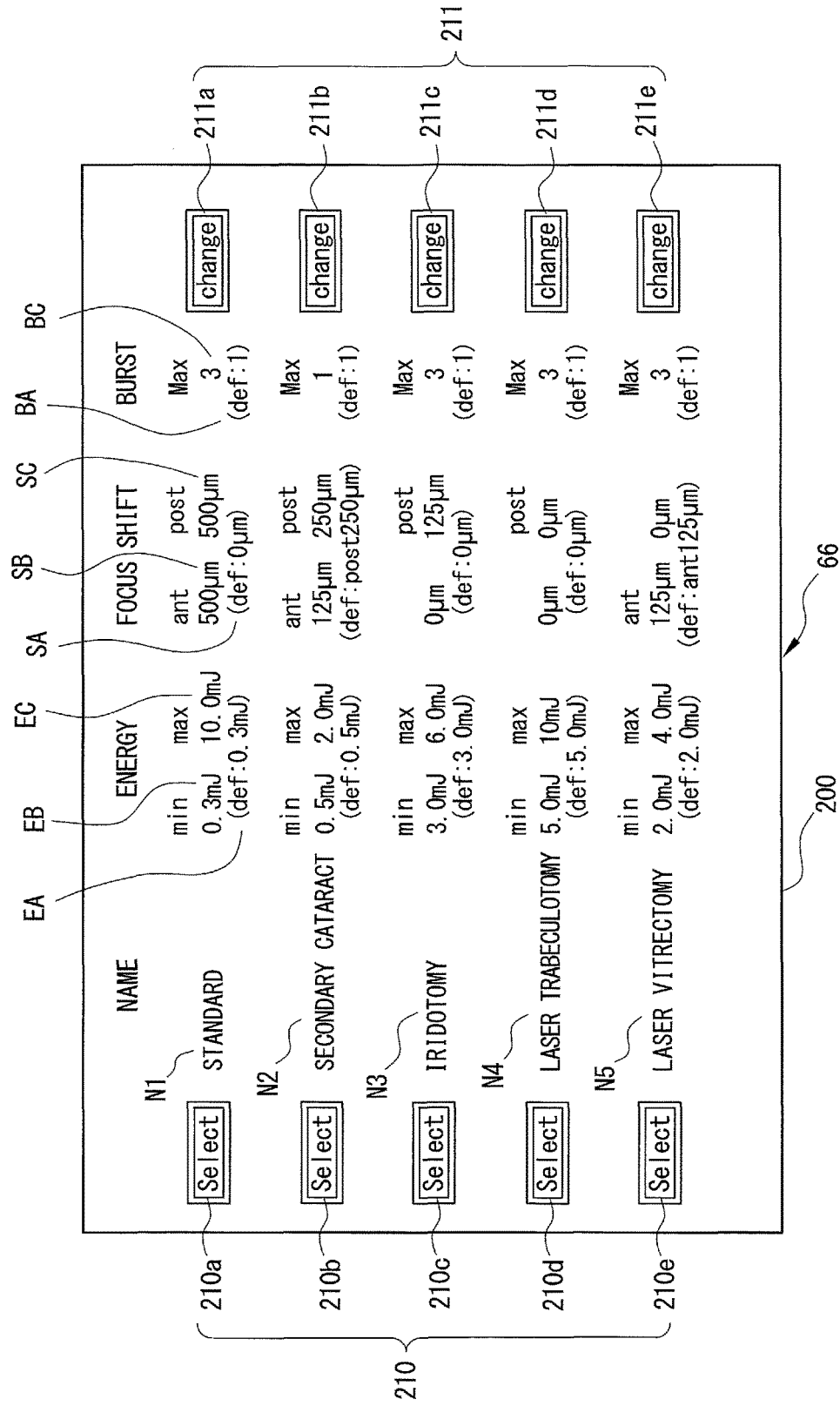
FIG. 3 is a diagram showing a selection screen displayed on the display unit.
Figure 4:
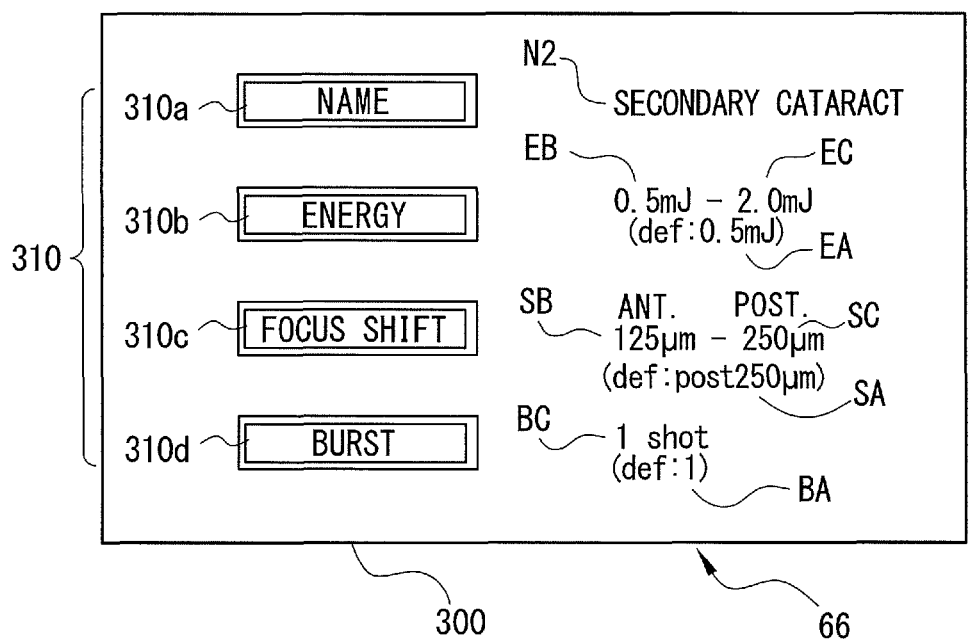
FIG. 4 is a diagram showing an edit screen displayed on the display unit.

Referring to FIGS. 2 to 4, display contents displayed on the display unit 66 in the present embodiment will be described below. The display unit 66 in the present embodiment has the touch panel function as mentioned above and serves as both the display unit and the input unit. The display unit 66 in the present embodiment selectively displays thereon a plurality of types of screens individually corresponding to the operation modes of the ophthalmic laser treatment apparatus 1. The ophthalmic laser treatment apparatus 1 in the present embodiment can cause the display unit 66 to display a treatment screen 100 (see FIG. 2), a selection screen 200 (see FIG. 3), and an edit screen 300 (see FIG. 4).

<Treatment Screen>

The treatment screen 100 in the present embodiment will be described referring to FIG. 2. FIG. 2 shows the treatment screen 100 for the secondary cataract mode as one example. In a field for irradiation energy amount on the treatment screen 100, a pair of adjustment buttons 117 (117a and 117b) are provided. In this irradiation energy amount field, further, an irradiation energy amount value 116 is displayed. The irradiation energy amount field is used for an operator to adjust the irradiation energy amount of a treatment laser beam. When the operator presses or touches the adjustment button(s) 117, a value appearing as the irradiation energy amount value 116 is changed. When the operator presses the trigger switch 67, a treatment laser beam of an energy amount (1 pulse) corresponding to the displayed value as the irradiation energy amount value 116 is irradiated to the patient's eye E.

In a field for focus shift position on the treatment screen 100, a pair of adjustment buttons 122 (122a and 122b) are provided. In this focus shift position field, a shift position value 121a and an image 121b are displayed. The focus shift position field is used for the operator to adjust a focus shift position. In the present embodiment, when the operator presses the adjustment button(s) 122, the shift position value 121a and the image 121b are changed. The image 121b indicates a shift direction of the focus shift position. The shift position value 121a represents a shift amount (distance) of the focus shift position. When the operator presses the adjustment button(s) 122, the focus shift position is immediately changed (the control unit 60 immediately drives the shift adjusting unit 50).

In a field for the number of bursts ("burst number") on the treatment screen 100, an adjustment button 119 is provided. In this burst number field, a burst number value 118 is displayed. This burst number field is used for the operator to adjust the number of bursts of a treatment laser beam. In the present embodiment, when the operator presses the adjustment button 119, a numerical value appearing as the burst number value 118 is changed. When the operator presses the trigger switch 67, a treatment laser beam (pulses) is intermittently irradiated to the patient's eye E by the number of times corresponding to the displayed numerical value as the burst number value 118.

In a filed for operation mode indicator on the treatment screen 100, an operation mode indicator 123 is displayed to indicate a current operation mode. In the present embodiment, as the operation mode indicator 123, the name of the current treatment mode is displayed in text. The operation mode display 123 may be displayed in the form of an icon corresponding to the type of the treatment mode.

In a field for menu button in the present embodiment, a menu button 126 is provided. When the operator presses the menu button 126, the display of the display unit 66 is changed to the selection screen 200.

<Selection Screen>

Referring to FIG. 3, the selection screen 200 in the present embodiment will be described below. On the selection screen 200, a treatment mode name and parameters related to irradiation of the treatment laser beam are displayed. On the selection screen 200, further, a plurality of selection buttons 210 (210a to 210e) and a plurality of edit buttons 211 (211a to 211e) are displayed. The treatment mode names (N1 to N5) are displayed in text corresponding to target disease cases. The parameters related to irradiation of the treatment laser beam include parameters related to the irradiation energy amount, parameters related to the focus shift position, and parameters related to the burst number.

On the selection screen 200, as the parameters related to the irradiation energy amount, there are displayed a default value EA of the irradiation energy amount, a lower limit EB to be used in adjusting the irradiation energy amount, and an upper limit EC to be used in adjusting the irradiation energy amount. On the selection screen 200, furthermore, as the parameters related to the focus shift position, there are displayed a default value SA of the focus shift position, an anterior position value SB which is a threshold on an anterior side in an adjustment range of the focus shift position, and a posterior position value SC which is a threshold on a posterior side in the adjustment range of the focus shift position. On the selection screen 200, still further, as the parameters related to the burst number, there are displayed a default value BA of the burst number and an upper limit BC to be used in adjusting the burst number. The foregoing various parameters are provided for each treatment mode. In the present embodiment, a lower limit to be used for adjustment of the burst number (i.e., a lower limit BB not shown) is fixed to 1.

The selection buttons 210 (210a to 210e) are provided for an operator to select each treatment mode. When the operator presses one of the selection buttons 210, the control unit 60 changes the display of the display unit 66 to the treatment screen 100 (see FIG. 2) and automatically sets the parameters related to irradiation of the treatment laser beam corresponding to the selected treatment mode. The edit buttons 211 (211a to 211e) are provided for the operator to edit the parameters in each treatment mode. When the operator presses one of the edit buttons 211, the display of the display unit 66 is changed to the edit screen 300 (see FIG. 4).

The selection screen 200 in the present embodiment as described above serves as a selection receiving unit for receiving an instruction to select any one of the plurality of treatment modes. The configuration of the selection receiving unit is not limited to the above one. As an alternative, the ophthalmic laser treatment apparatus 1 has only to receive an instruction to select any one of the plurality of treatment modes. For instance, selection of a treatment mode may be performed by an information processing terminal connected to the ophthalmic laser treatment apparatus 1. In this case, the control unit 60 that receives a signal from the information processing terminal (a signal representing the treatment mode) serves as the selection receiving unit. As another alternative, for instance, the display unit 66 may include a control unit (CPU, ROM, RAM, etc.) so that the control unit of the display unit 66 transmits a treatment mode selected on the selection screen 200 to the control unit 60. In this case, the selection screen 200 serves as the selection receiving unit. Further, the control unit 60 serves as the selection receiving unit for receiving a signal (a signal related to the treatment mode) from the display unit 66 as with the foregoing information processing terminal. It is to be noted that an operation button, a mouse, a keyboard, a joystick and others may be used as the selection receiving unit.

<Edit Screen>

The edit screen 300 in the present embodiment will be described below referring to FIG. 4. FIG. 4 shows, as one example, the case where an operator presses the edit button 211b (corresponding to the secondary cataract mode) on the selection screen 200. On the edit screen 300, there are displayed a treatment mode name N2, parameters related to the irradiation energy amount (default value EA, lower limit EB, and upper limit EC), parameters related to the focus shift position (default value SA, anterior position value SB, and posterior position value SC), and parameters related to the burst number (default value BA and upper limit BC). On the edit screen 300, a plurality of change buttons 310 (310a to 310d) are further displayed.

Specifically, the ophthalmic laser treatment apparatus 1 includes the nonvolatile memory 65 that stores values of parameters related to irradiation of the treatment laser beam. This nonvolatile memory 65 stores parameters related to irradiation of a plurality of treatment laser beams individually corresponding to the plurality of treatment modes. Herein, values of the parameters related to irradiation of the plurality of treatment laser beams can be edited by use of the edit screen 300. The operator can readily change various conditions for suitably operating the ophthalmic laser treatment apparatus 1 in the above manner. Since the operation conditions of the ophthalmic laser treatment apparatus 1 are displayed on the screens, the operator can easily ascertain the operation conditions of the ophthalmic laser treatment apparatus 1.

<Parameters>

The ophthalmic laser treatment apparatus 1 in the present embodiment stores the parameters related to irradiation of the treatment laser beam in the nonvolatile memory 65 as described above. In the present embodiment, the parameters for each of five treatment modes are stored in the nonvolatile memory 65. The control unit 60 retrieves the information on the parameters for the selected treatment mode from the nonvolatile memory 65 and uses that information in various controls of the ophthalmic laser treatment apparatus I including irradiation of the treatment laser beam and others. The operator can rewrite the parameters stored in the nonvolatile memory 65 by operation on the edit screen 300.

There is described below one example that the foregoing parameters are used in control of the ophthalmic laser treatment apparatus 1. The default value EA corresponds to the irradiation energy amount value 116 on the treatment screen 100. The lower limit EB and the upper limit EC are not displayed on the treatment screen 100. However, these values may be used when an operator adjusts the irradiation energy amount value 116 on the treatment screen 100. To be specific, when the operator is operating the treatment screen 100 to change the irradiation energy amount to a smaller value (a larger value) than the lower limit EB (the upper limit EC), the control unit 60 notifies the operator of the lower limit EB and the upper limit EC. That is, a range from the lower limit EB to the upper limit EC is defined as an adjustment range in which the irradiation energy amount can be adjusted by the operator.

The default value SA corresponds to the shift position value 121a and the image 121b of the treatment screen 100. The anterior position value SB and the posterior position value SC are not displayed on the treatment screen 100. However, these values may be used when the operator adjusts the focus shift position on the treatment screen 100. To be specific, when the operator is operating the treatment screen 100 to change the focus shift position to a more anterior position (a more posterior position) than the anterior position value SB (the posterior position value SC), the control unit 60 notifies the operator of the anterior position value SB and the posterior position value SC. That is, a range from the anterior position value SB to the posterior position value SC is defined as an adjustment range in which the focus shift position can be adjusted by the operator.

The default value BA corresponds to the burst number value 118 on the treatment screen 100. The lower limit BB and the upper limit BC are not displayed on the treatment screen 100. However, these values may be used when the operator adjusts the burst number on the treatment screen 100. To be specific, when the operator is operating the treatment screen 100 to change the burst number to a larger number than the upper limit BC, the control unit 60 notifies the operator of the upper limit BC. Specifically, natural numbers up to the upper limit BC are defined as an adjustment range in which the number of bursts can be adjusted by the operator.

Figure 5:
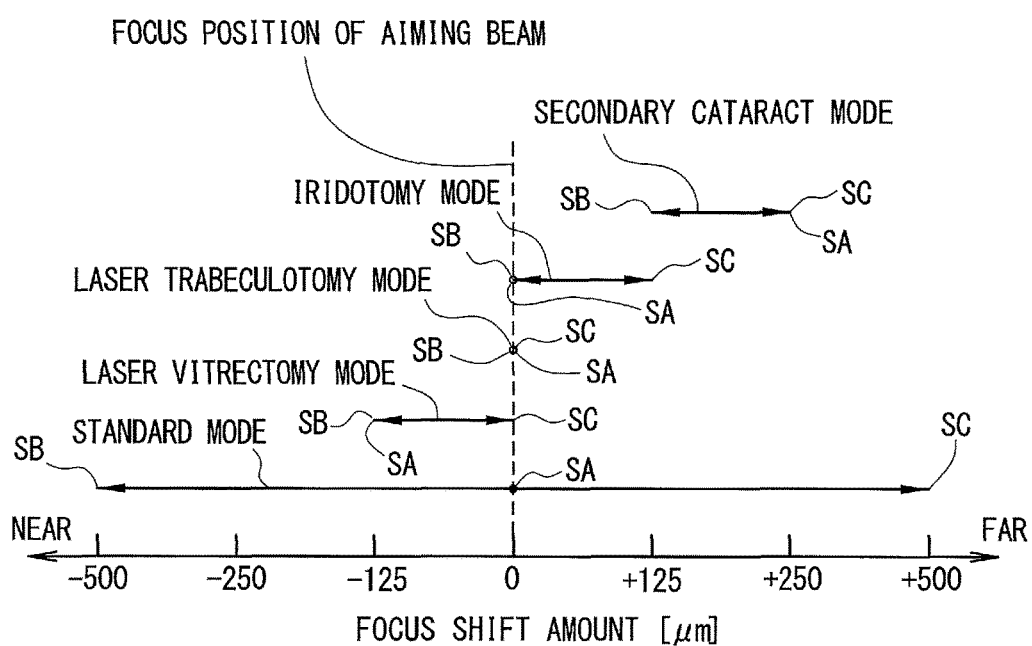
FIG. 5 is an explanatory diagram to explain a relationship between parameters in the embodiment.

Referring to FIGS. 3 and 5, the characteristics of the parameters of each treatment mode in the present embodiment will be explained below. In the present embodiment, a range in which a parameter can be adjusted without notification is defined as an adjustment range of that parameter. When the secondary cataract mode is selected, the control unit 60 sets the adjustment range of the focus shift position (the anterior position value SB to the posterior position value SC) in a range more posterior than the focus position of the aiming beam. In other words, when the treatment mode (for example, secondary cataract mode) of treating a more anterior portion than the vitreous body is selected in the present embodiment, the control unit 60 sets the focus shift position at a more posterior position than the focus position of the aiming beam. This can appropriately prevent, in an secondary cataract surgery for example, an intraocular lens positioned on a nearer side than an opacified posterior capsule of a crystalline lens from getting accidentally damaged by the treatment laser beam.

Furthermore, when any one of the iridotomy mode, the laser trabeculotomy mode, and the laser vitrectomy mode is selected, the control unit 60 provides the adjustment range (anterior position value SB to posterior position value SC) of the focus shift position on a more anterior side than the adjustment range (anterior position value SB to posterior position value SC) of the focus shift position set when the secondary cataract mode is selected. In the present embodiment, when the treatment mode of treating a more posterior portion than a lens posterior capsule (for example, the laser vitrectomy mode) is selected, the control unit 60 sets the focus shift position on a more anterior side than the focus position of the aiming beam. This can appropriately prevent, in the laser vitrectomy mode for example, a retina of a patient's eye from getting accidentally damaged by the treatment laser beam. It is to be noted that, as the treatment mode of treating the more posterior portion than the lens posterior capsule, there may be provided a vitreous floater treatment mode in which a treatment laser beam is irradiated to an opacified portion of a vitreous body of a patient's eye. Also in this vitreous floater treatment mode, the control unit 60 sets the focus shift position on a more anterior side than the focus position of the aiming beam. This can appropriately suppress accidental damage of a retina of the patient's eye by the treatment laser beam.

The ophthalmic laser treatment apparatus 1 in the present embodiment as described above can suppress an adverse event for instance that the operator directs the treatment laser beam at an undesired position (in the anterior-posterior direction) without taking notice of incorrect setting. Thus, a burden on a patient's living body can be reduced. Further, the treatment laser beam can be efficiently irradiated to an affected part. Accordingly, for instance, the operator can promptly treat the affected part.

When the secondary cataract mode is selected, the control unit 60 adjusts the focus shift position (the default value SA) of the treatment laser beam to the same position as the focus position of the aiming beam or to the more posterior position than the focus position of the aiming beam. This can suppress for example any adverse influence of the treatment laser beam on the intraocular lens. When the secondary cataract treatment mode is changed to any one of the iridotomy mode, the laser trabeculotomy mode, and the laser vitrectomy mode, the control unit 60 adjusts the focus shift position (default value SA) of the treatment laser beam to the more anterior position than the focus shift position (default value SA) having been set in the secondary cataract mode. This can suppress an adverse event for instance that the operator directs the treatment laser beam at an undesired position (in the anterior-posterior direction) without taking notice of incorrect setting. Thus, a burden on a patient's living body can be reduced. Further, the treatment laser beam can be efficiently irradiated to an affected part. Accordingly, for instance, the operator can promptly treat the affected part.

<How to Use>

Figure 6:
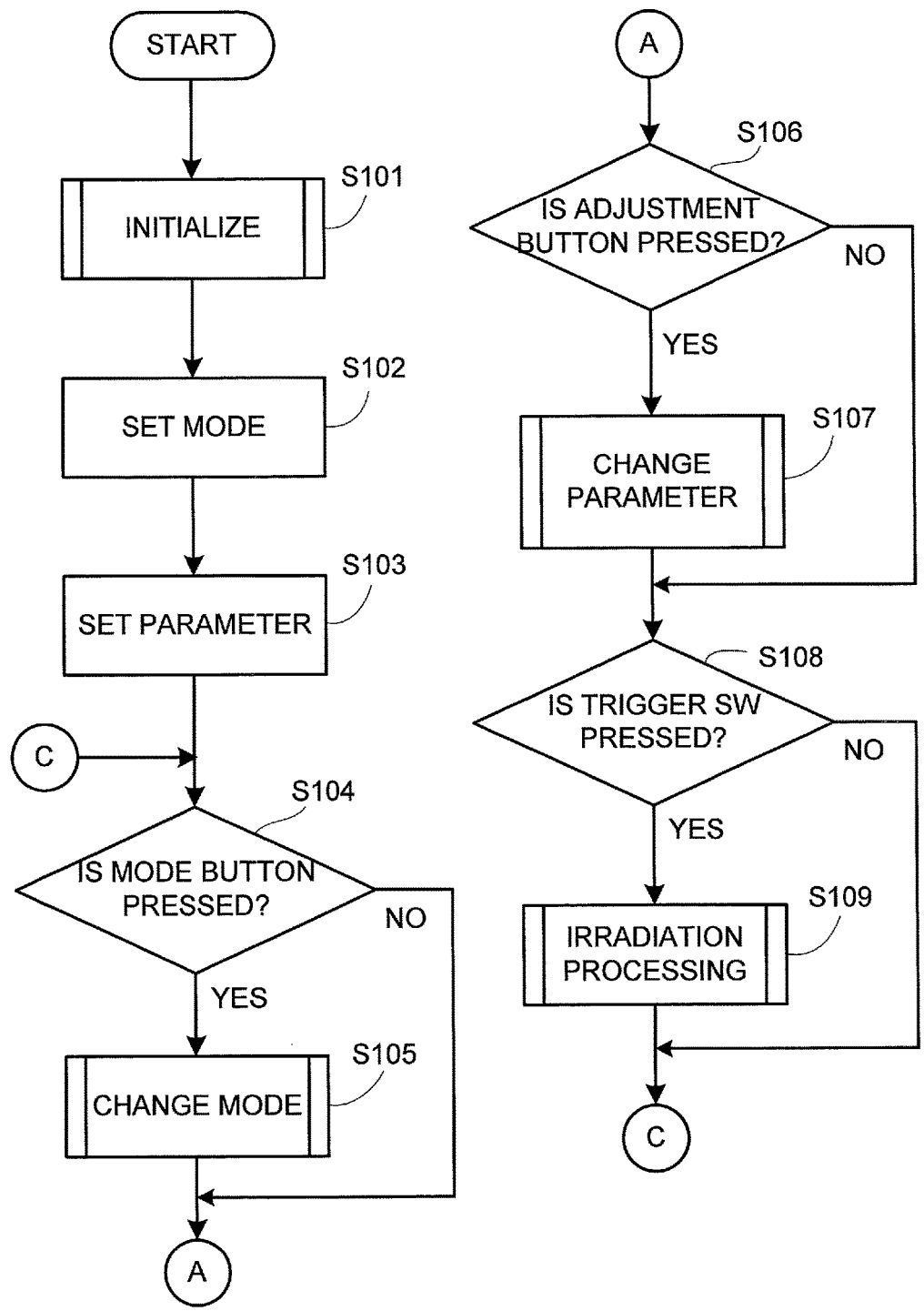
FIG. 6 is a flowchart related to control of the ophthalmic laser treatment apparatus.
Figure 7:
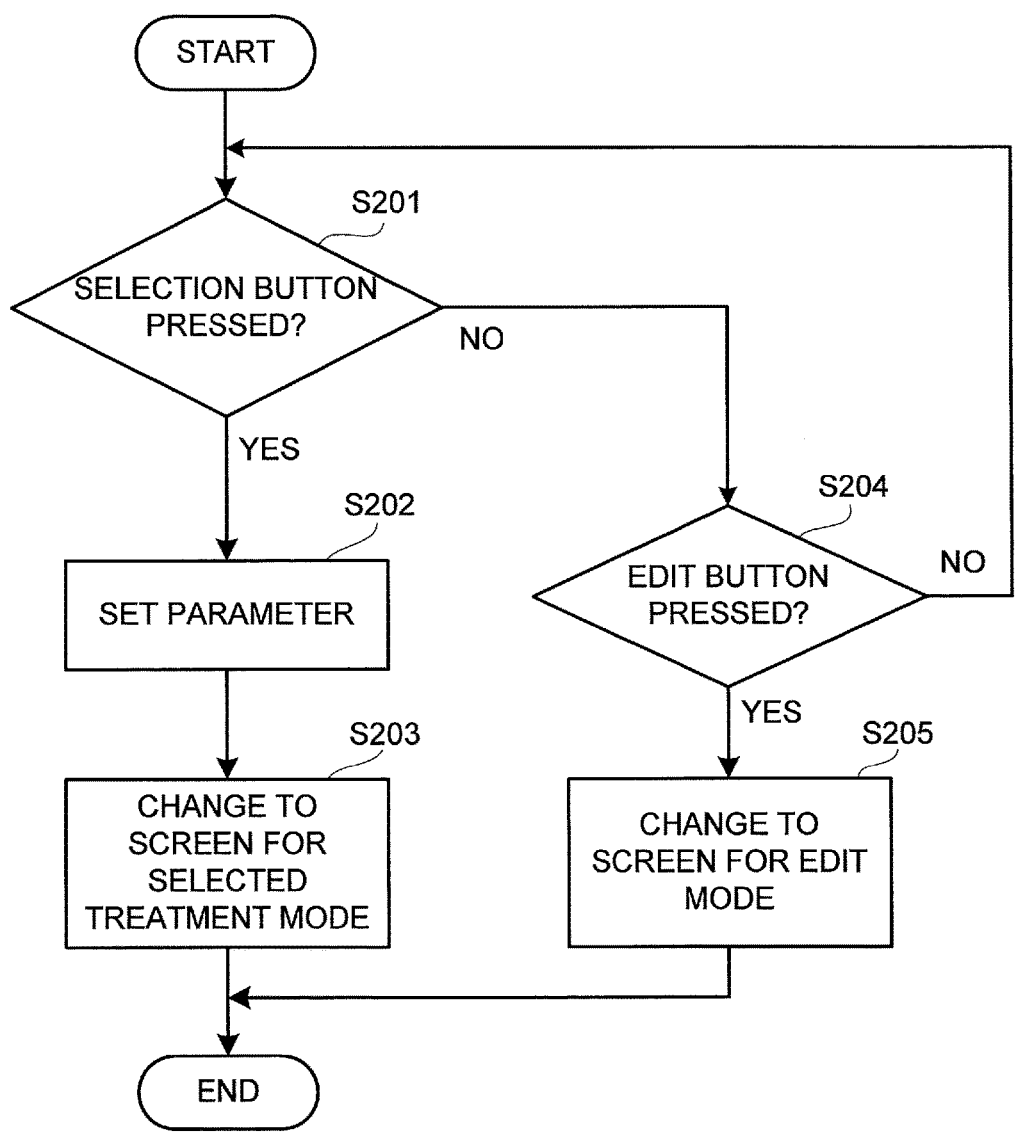
FIG. 7 is a flowchart related to control during mode change.
Figure 8:
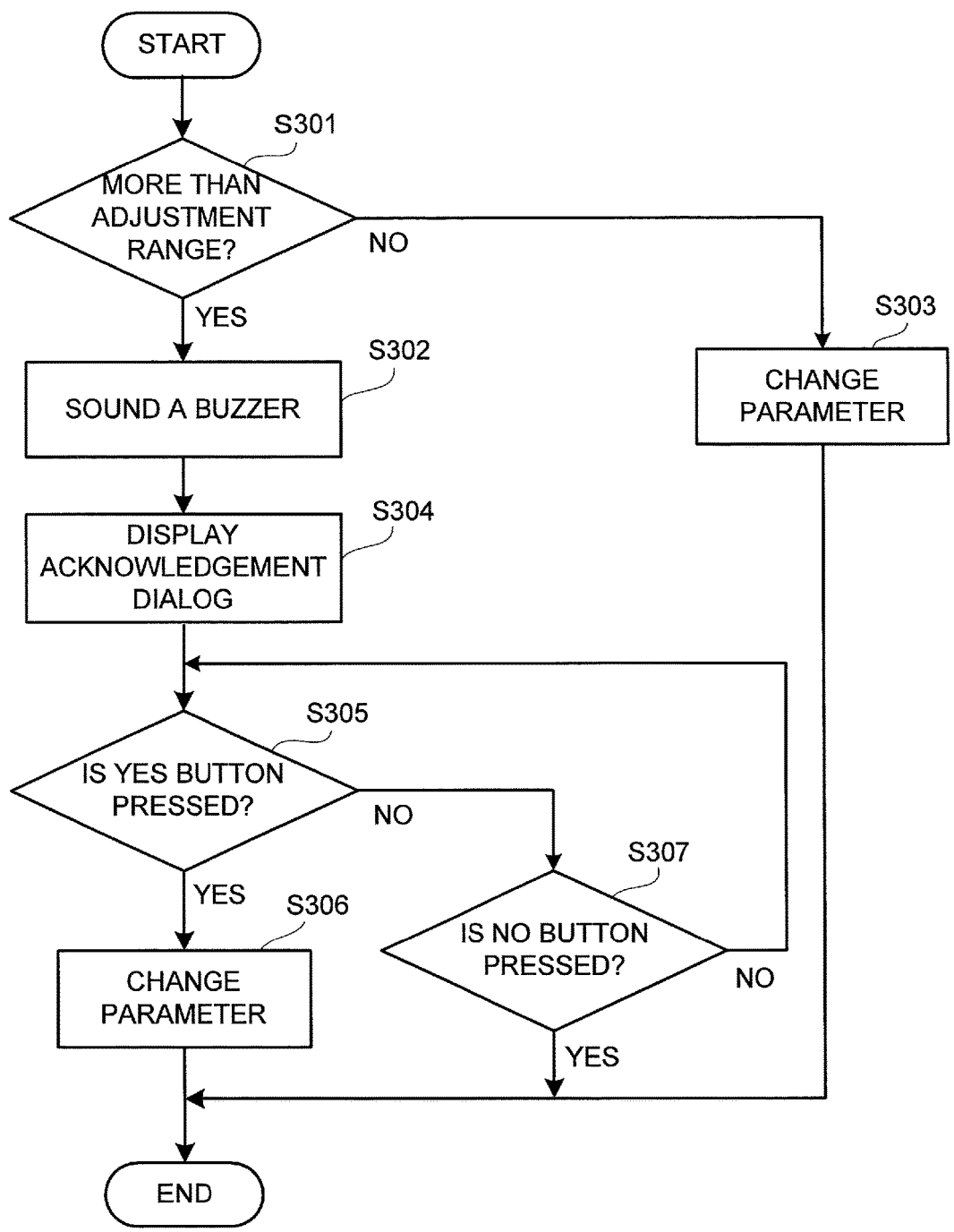
FIG. 8 is a flowchart related to control during manual operation.

Referring to FIGS. 6 to 8, one example of how to use the ophthalmic laser treatment apparatus 1 in the present embodiment will be described below. An operator turns on the power of the ophthalmic laser treatment apparatus 1. At power-on, the control unit 60 executes initialization (see step S101). For instance, as the process of initialization, operation check of the safety shutter 19 and other checks may be executed. The control unit 60 goes on to set the operation mode of the ophthalmic laser treatment apparatus 1 to the standard mode (see step S102).

The control unit 60 then sets various parameters for the standard mode (step S103). The various parameters include parameters related to the treatment laser beam, parameters related to the focus shift position, and parameters related to the number of bursts. More specifically, the various parameters includes the default value EA, the lower limit EB, the upper limit EC, the default value SA, the anterior position value SB, the posterior position value SC, the default value BA, the lower limit BB, and the upper limit BC (for each value, see FIG. 3 and others). The control unit 60 displaces the focus shift position at the time of setting various parameters. The control unit 60 successively irradiates the aiming beam to a patient's eye E. The various parameters in the present embodiment include the irradiation energy amount. In the present embodiment, when the various parameters are set in step S103 or S107, the control unit 60 adjusts the angle of the ½ wave plate 14. More specifically, the control unit 60 drives the motor 15 of the energy adjusting unit 13 based on values of the various parameters set as above to adjust the angle of the ½ wave plate 14 to an angle corresponding to the irradiation setting. In the present embodiment, namely, the angle of the ½ wave plate 14 is adjusted before the trigger switch 67 is pressed to cause the control unit 60 to start the irradiation control of the treatment laser beam (before step S108).

The control unit 60 then displays the treatment screen 100 on the display unit 66. On the treatment screen 100, the default values (default value EA, default value SA, and default value BA) of the parameters set for the standard mode are displayed. In step S102 mentioned above, the control unit 60 may set another treatment mode. As an alternative, the control unit 60 may perform control of allowing the operator to select a treatment mode.

The operator changes the treatment mode or adjusts various parameters according to a treatment purpose on the patient's eye E (see steps S104, S105, S106, and S107). The operator aligns the aiming beam with the affected part of the patient's eye E and then presses the trigger switch 67. When the trigger switch 67 is pressed, the control unit 60 causes the treatment laser beam to be irradiated to the patient's eye E at the values of the various parameters set in advance (see step S109). In detail, the control unit 60 controls the irradiation of the treatment laser beam under the conditions corresponding to the irradiation energy amount value 116, the shift position value 121a, the image 121b, and the burst number value 118 which are displayed on the display unit 66.

Herein, when the operator presses the menu button 126 on the treatment screen 100, the control unit 60 causes the display unit 66 to display the selection screen 200 (see step S104). With this selection screen 200, the operator selects the treatment mode corresponding to the disease case of the patent's eye E (see FIG. 3). When the treatment mode is selected by the operator, the control unit 60 sets parameters related to irradiation of the treatment laser beam corresponding to the selected disease case (the treatment mode) and then causes the display unit 66 to display the treatment screen 100 (see S201 to S203 in FIG. 7). More specifically, as the parameters related to the irradiation of the treatment laser beam, the default value EA, the lower limit EB, the upper limit EC, the default value SA, the anterior position value SB, the posterior position value SC, the default value BA, the lower limit BB, and the upper limit BC are set (for each value, see FIG. 3 and others). In other words, the control unit 60 sets values of the parameters related to the irradiation of the treatment laser beam including the parameters related to the shift of the focus shift position according to the treatment mode selected on the selection screen 200 (see FIGS. 3 and 7). The control unit 60 further changes the values (default value EA, lower limit EB, and upper limit EC) related to the irradiation energy amount included in the parameters related to the irradiation of the treatment laser beam, according to the treatment mode selected on the selection screen 200.

Herein, the parameters related to the shift of the focus shift position include the adjustment range of the focus shift position. The control unit 60 sets the adjustment range of the focus shift position according to the treatment mode selected on the selection screen 200. The control unit 60 further sets the values (in the present embodiment, the default value SA) of parameters representing the focus shift position according to the treatment mode selected on the selection screen 200. In the present embodiment, the control unit 60 drives the motor 55 to change the focus shift position at the time of setting the parameters related to the irradiation of the treatment laser beam. That is, the control unit 60 drives the motor 55 according to the values (in the present embodiment, the default value SA) of parameters representing the focus shift position.

When the operator presses one of the edit buttons 211 on the selection screen 200, the control unit 60 causes the display unit 66 to display the edit screen 300 (see step S204 and S205). On the edit screen 300, the parameters related to the irradiation of the treatment laser beam are displayed. The displayed parameters correspond to the edit buttons 211 (211a to 211e) pressed on the selection screen 200 by the operator. The operator presses the change button(s) 310 (310a to 310d) as necessary to change the value(s) of parameter(s). When the value(s) of parameter(s) is changed, the control unit 60 causes the display unit 66 to display the selection screen 200.

Next, the following explanation will be given to a case where the operator adjusts the irradiation energy amount value 116, the shift position value 121a and the image 121b, or the burst number value 118 on the treatment screen 100. In the present embodiment, two types of adjustment ranges are provided for each parameter. Specifically, each of the irradiation energy amount, the focus shift position, and the number of bursts includes a first adjustment range and a second adjustment range. The first adjustment range in the present embodiment corresponds to an adjustable range in the standard mode. The second adjustment range in the present embodiment is equal to the adjustable range in the standard mode or is smaller than the adjustable range in the standard mode. In the present embodiment, the second adjustment range corresponds to values (the lower limit EB, the upper limit EC, the anterior position value SB, the posterior position value SC, and the upper limit BC) displayed on the selection screen 200.

One example of adjusting the irradiation energy amount after the secondary cataract mode is selected by the operator will be described below. When the irradiation energy amount changed by operation of the adjustment button(s) by the operator falls outside the above-described second adjustment range (it is less than the lower limit EB or more than the upper limit EC), the control unit 60 sounds the buzzer 68 for notification to the operator (see step 5302 in FIG. 8). In other words, when the focus shift position shifted by the shift adjusting unit 50 falls outside the adjustment range (the second adjustment range) set according to the treatment mode, the control unit 60 sounds the buzzer 68. Continuously, the control unit 60 displays an acknowledgement dialog on the display unit 66 (step S304). In this acknowledgement dialog, a message to be notified and a YES button and a NO button are displayed. If the change is as intended, the operator presses the YES button in the acknowledgement dialog. When the YES button is pressed, the control unit 60 changes the parameter(s) (see step S306). In contrast, if the operator abandons changing the parameter beyond the adjustable range, the operator presses the NO button in the acknowledgement dialog.

In the above manner, it is possible to suppress an adverse event for instance that the operator incorrectly sets a parameter(s) relating to the treatment laser beam. A method of providing notification to the operator may be similar between when the parameter exceeds the first adjustment range and when the parameter exceeds the second adjustment range. In the above description, the irradiation energy amount is adjustable outside the second adjustment range, but it may be arranged to disable adjusting the irradiation energy amount outside the second adjustment range. Although the above description shows adjustment of the irradiation energy amount, but the focus shift position and the number of bursts are also subjected to the same control in the present embodiment.

<Operations and Advantageous Effects>

The ophthalmic laser treatment apparatus 1 in the present embodiment includes the aiming optical system 20 for irradiating the aiming beam to a patient's eye E, the laser irradiation optical system 10 for irradiating the laser beam for treatment to the patient's eye E, the shift adjusting unit 50 (the shift unit) for making a shift of the focus shift position corresponding to the focus position of the laser beam to a posterior position or an anterior position with respect to the focus position of the aiming beam, the selection screen 200 (the selection receiving unit) for receiving an instruction to select any one of the plurality of treatment modes, and the control unit 60 (the control unit) for controlling operations of the ophthalmic laser treatment apparatus 1. Herein, the control unit 60 sets the value(s) of the parameter(s) related to irradiation of the laser beam (for example, in the present embodiment, at least one of the default value EA, the lower limit EB, the upper limit EC, the default value SA, the anterior position value SB, the posterior position value SC, the default value BA, the lower limit BB, and the upper limit BC) including the parameter (for example, in the present embodiment, at least one of the default value SA, the anterior position value SB, and the posterior position value SC) related to the shift of the focus shift position, according to the treatment mode selected with the selection receiving unit. For instance, this makes it easy for an operator to easily operate the ophthalmic laser treatment apparatus 1. Further, the operator is less likely to incorrectly set the parameters related to irradiation of the laser beam. Accordingly, the operator can also promptly perform a treatment on an affected part with the ophthalmic laser treatment apparatus 1.

The parameters included in the ophthalmic laser treatment apparatus 1 in the present embodiment related to the shift of the focus shift position includes the adjustment range of the focus shift position. The control unit sets the adjustment range of the focus shift position according to the treatment mode selected with the selection receiving unit. Accordingly, for example, the operator is less likely to incorrectly set the focus shift position. Further, the operator can promptly set the focus shift position.

The ophthalmic laser treatment apparatus 1 in the present embodiment further includes the buzzer 68 (one example of a notification unit) to provide notification to the operator. When the focus shift position shifted by the shift unit falls outside the adjustment range set according to the treatment mode, the control unit causes the notification unit to provide notification. Accordingly, for example, the operator is further less likely to incorrectly set the focus shift position. Thus, even the operator who is not familiar with handling the ophthalmic laser treatment apparatus 1 can promptly adjust the focus shift position.

In the ophthalmic laser treatment apparatus 1 in the present embodiment, when an secondary cataract treatment mode is selected from the plurality of treatment modes with the selection receiving unit, the control unit sets the adjustment range of the focus shift position in a more posterior range than the focus position of the aiming beam). Accordingly, for instance, the focus shift position can be promptly adjusted in the secondary cataract treatment mode. The operator is further less likely to incorrectly set the focus shift position. Specifically, in the secondary cataract surgery, it is possible to appropriately prevent an intraocular lens positioned on a nearer side than an opacified posterior capsule of a crystalline lens from getting accidentally damaged by the treatment laser beam.

In the ophthalmic laser treatment apparatus 1 in the present embodiment, when the treatment mode of executing any one of iridotomy, laser trabeculotomy, and laser vitrectomy is selected with the selection receiving unit, the control unit sets the adjustment range of the focus shift position in a more anterior range than the adjustment range set when the secondary cataract treatment mode is selected. Accordingly, for instance, laser treatment can be promptly performed with respect to different types of disease cases. In addition, the focus shift position is less likely incorrectly set.

The parameter related to the shift of the focus shift position to be used in the ophthalmic laser treatment apparatus 1 in the present embodiment includes a value of a parameter representing the focus shift position. The control unit sets the value of the parameter representing the focus shift position according to the treatment mode selected with the selection receiving unit. Accordingly, even an operator who is not familiar with handing the ophthalmic laser treatment apparatus 1 can appropriately adjust the focus shift position. The focus shift position is also less likely incorrectly set.

The ophthalmic laser treatment apparatus 1 in the present embodiment further includes the drive unit for driving the shift unit to make a shift of the focus shift position. The control unit drives the drive unit according to the value of the parameter representing the focus shift position set according to the treatment mode. Accordingly, for instance, the operator can quickly set the focus shift position. In addition, for example, the time required for treatment can be shortened.

In the ophthalmic laser treatment apparatus 1 in the present embodiment, when an secondary cataract treatment mode is selected from the plurality of treatment modes with the selection receiving unit, the control unit sets the value of parameter representing focus shift position so that the focus shift position of the laser beam is located at the same position as the focus position of the aiming beam or at a more posterior position than the focus position of the aiming beam. Accordingly, for instance, incorrect setting of the focus shift position can be appropriately suppressed. For instance, it is possible to appropriately prevent an adverse event that a treatment laser beam is irradiated to an intraocular lens during secondary cataract surgery.

In the ophthalmic laser treatment apparatus 1 in the present embodiment, when an secondary cataract treatment mode is changed with the selection receiving unit to any one of the treatment modes for iridotomy, laser trabeculotomy, and laser vitrectomy, the control unit changes the value of the parameter representing the focus shift position so that the focus shift position of the laser beam is located at an anterior position than the focus shift position set in the secondary cataract mode. Accordingly, an operation time required to adjust the focus shift position according to the disease case can be shortened. With the ophthalmic laser treatment apparatus 1, therefore, prompt treatment of an affected part of a patient's eye can be achieved.

The ophthalmic laser treatment apparatus 1 of the present embodiment further includes a storage unit for storing the value(s) of the parameter(s) related to irradiation of the laser beam. The storage unit stores parameters related to irradiation of a plurality of the laser beams corresponding to each of the plurality of treatment modes. The ophthalmic laser treatment apparatus 1 further includes an edit unit for editing values of the parameters related to irradiation of the plurality of the laser beams. Accordingly, for example, the ophthalmic laser treatment apparatus 1 can be used with parameter setting(s) desired by the operator. In addition, the parameters related to irradiation of the treatment laser beam are automatically changed to other values according to the selected treatment mode. Thus, the ophthalmic laser treatment apparatus 1 can be appropriately used.

The parameter related to irradiation of the laser beam to be used by the ophthalmic laser treatment apparatus 1 in the present embodiment includes the irradiation energy amount of the laser beam. The control unit changes the value related to the irradiation energy amount included in the parameter related to the irradiation of the laser beam according to the treatment mode selected with the selection receiving unit. Accordingly, it is possible to reduce the time and trouble required to change the treatment mode.

The control unit may be configured to actuate the display unit 66 to display a recommended value to recommend a focus shift position suitable for the selected treatment mode to a user. In this case, the control unit may display the recommended value by a value of the parameter representing the focus shift position set according to the treatment mode. Accordingly, for example, even if the ophthalmic laser treatment apparatus 1 is not provided with the motor 55, the operator can manually adjust the focus shift position to an appropriate position while checking the aforementioned recommended value.

It should be understood that the embodiment in this disclosure is a mere example in all respects and is not limitative. The scope of the invention is specified in claims not in the above description and is intended to include all changes or modifications in the claims and equivalent meanings thereto.

What is claimed is:

1. An ophthalmic laser treatment apparatus comprising:
an aiming optical system configured to irradiate an aiming beam to a patient's eye;
a laser irradiation optical system configured to irradiate a laser beam for treatment to the patient's eye;
a shift unit configured to shift a focus shift position, which corresponds to a focus position of the laser beam, between maximum posterior and maximum anterior positions with respect to a focus position of the aiming beam;
a drive unit configured to drive the shift unit to shift the focus shift position;
a selection receiving unit configured to receive an instruction to select any one of a plurality of treatment modes; and
a processor and associated memory configured to control operations of the ophthalmic laser treatment apparatus, wherein:
the processor sets, according to the treatment mode selected with the selection receiving unit, a value of at least one parameter related to irradiation of the laser beam, and
the at least one parameter includes a parameter that includes an adjustment range of the focus shift position, the adjustment range being within and different from a maximum range of the focus shift position that is bounded by the maximum posterior and maximum anterior positions.

2. The ophthalmic laser treatment apparatus according to claim 1, further comprising a notification unit to provide notification to an operator,
wherein when the focus shift position shifted by the shift unit falls outside the adjustment range set according to the treatment mode, the processor causes the notification unit to provide notification.

3. The ophthalmic laser treatment apparatus according to claim 1, wherein when a secondary cataract treatment mode is selected from the plurality of treatment modes with the selection receiving unit, the processor sets the adjustment range of the focus shift position in a more posterior range than the focus position of the aiming beam.

4. The ophthalmic laser treatment apparatus according to claim 3, wherein when a treatment mode of executing any one of iridotomy, laser trabeculotomy, and laser vitrectomy is selected with the selection receiving unit, the processor sets the adjustment range of the focus shift position in a more anterior range than the adjustment range set when the secondary cataract treatment mode is selected.

5. The ophthalmic laser treatment apparatus according to claim 1, wherein the at least one parameter related to the irradiation of the laser beam includes a value of a parameter representing the focus shift position, and
the processor sets the value of the parameter representing the focus shift position according to the treatment mode selected with the selection receiving unit.

6. The ophthalmic laser treatment apparatus according to claim 5,
wherein the processor drives the drive unit according to the value of the parameter representing the focus shift position set according to the treatment mode.

7. The ophthalmic laser treatment apparatus according to claim 5, wherein when a secondary cataract treatment mode is selected from the plurality of treatment modes with the selection receiving unit, the processor sets the value of the parameter representing the focus shift position so that the focus shift position of the laser beam is located at a same position as the focus position of the aiming beam or a more posterior position than the focus position of the aiming beam.

8. The ophthalmic laser treatment apparatus according to claim 7, wherein when the secondary cataract treatment mode is changed with the selection receiving unit to any one of treatment modes for iridotomy, laser trabeculotomy, and laser vitrectomy, the processor changes the value of the parameter representing the focus shift position so that the focus shift position of the laser beam is located at a more anterior position than the focus shift position set in the secondary cataract mode.

9. The ophthalmic laser treatment apparatus according to claim 1, wherein:
   the memory is configured to store the value of the at least one parameter related to irradiation of the laser beam so that parameters related to irradiation of a plurality of the laser beams are stored in correspondence to each of the plurality of treatment modes; and
   the processor is further configured to edit values of the parameters related to irradiation of the plurality of the laser beams.

10. The ophthalmic laser treatment apparatus according to claim 1, wherein:
   the at least one parameter related to irradiation of the laser beam includes an irradiation energy amount of the laser beam, and
   the processor changes a value related to the irradiation energy amount according to the treatment mode selected with the selection receiving unit.

* * * * *